United States Patent

Schmitz

[11] Patent Number: 5,853,404
[45] Date of Patent: Dec. 29, 1998

[54] DISPOSABLE ABSORBENT ARTICLE HAVING A FOLDED LANDING MEMBER FOR ENGAGING WITH A HOOK-TYPE FASTENING MEMBER

[75] Inventor: Christoph Johann Schmitz, Euskirchen-Stotzheim, Germany

[73] Assignee: The Procter & Gamble Company, Cincinnati, Ohio

[21] Appl. No.: 894,294

[22] PCT Filed: Jan. 30, 1996

[86] PCT No.: PCT/US96/01192

§ 371 Date: Aug. 15, 1997

§ 102(e) Date: Aug. 15, 1997

[87] PCT Pub. No.: WO96/25132

PCT Pub. Date: Aug. 22, 1996

[30] Foreign Application Priority Data

Feb. 16, 1995 [EP] European Pat. Off. ............ 95102143.5

[51] Int. Cl.[6] ............................................. A61F 13/15
[52] U.S. Cl. ............................................. 604/386; 604/391
[58] Field of Search ........................... 604/385.1, 386, 604/387, 391

[56] References Cited

U.S. PATENT DOCUMENTS

| | | |
|---|---|---|
| 3,860,003 | 1/1975 | Buell . |
| 4,699,622 | 10/1987 | Toussant et al. ..................... 604/389 |
| 4,762,521 | 8/1988 | Roessler et al. ................... 604/385.1 |
| 4,769,023 | 9/1988 | Goebel et al. ..................... 604/385.1 |
| 4,916,005 | 4/1990 | Lippert et al. .................... 604/385.1 |
| 5,112,326 | 5/1992 | Quadrini .......................... 604/385.1 |
| 5,318,555 | 6/1994 | Siebers et al. ................... 604/385.1 |
| 5,763,041 | 6/1998 | Leak et al. ........................... 604/393 |
| 5,785,699 | 7/1998 | Schmitz ............................... 604/391 |
| 5,795,350 | 8/1998 | Schmitz ............................... 604/391 |
| 5,797,896 | 8/1998 | Schmitz ............................... 604/391 |

FOREIGN PATENT DOCUMENTS 0 321 234 A  6/1989  European Pat. Off. .
1 458 566  12/1976  United Kingdom .

Primary Examiner—Mark O. Polutta
Attorney, Agent, or Firm—David M. Weirich; Steven W. Miller; Jacobus C. Rasser

[57] ABSTRACT

The invention relates to an absorbent article having two hook-type fastening members and a loop-type landing member in the front waist region, which is formed by a doubled over part of an inner layer that is located on the user facing side of the backsheet. The doubled over inner layer may for instance be comprised of the topsheet and may extend beyond the front transverse edge of the backsheet or may be co-extensive with the backsheet. The front waist region is maintained in a doubled over configuration by attachment means.

18 Claims, 8 Drawing Sheets

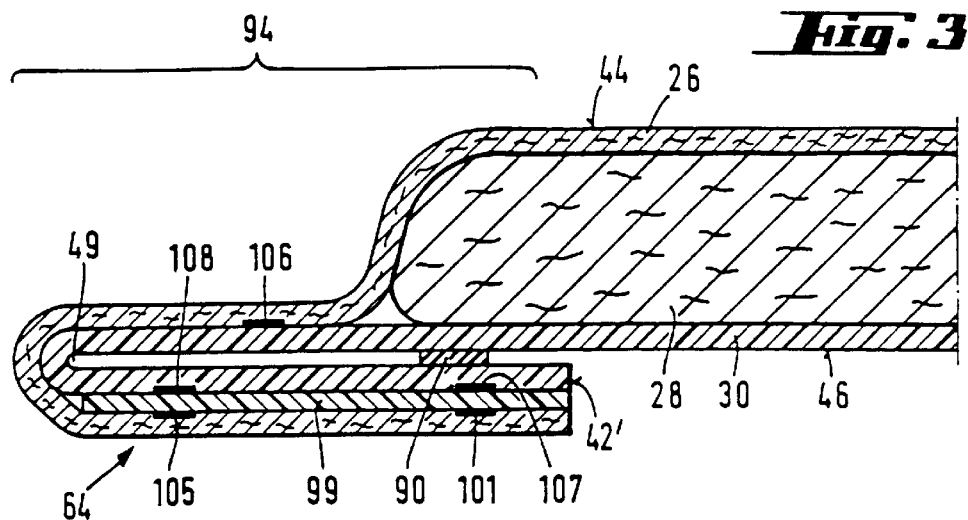
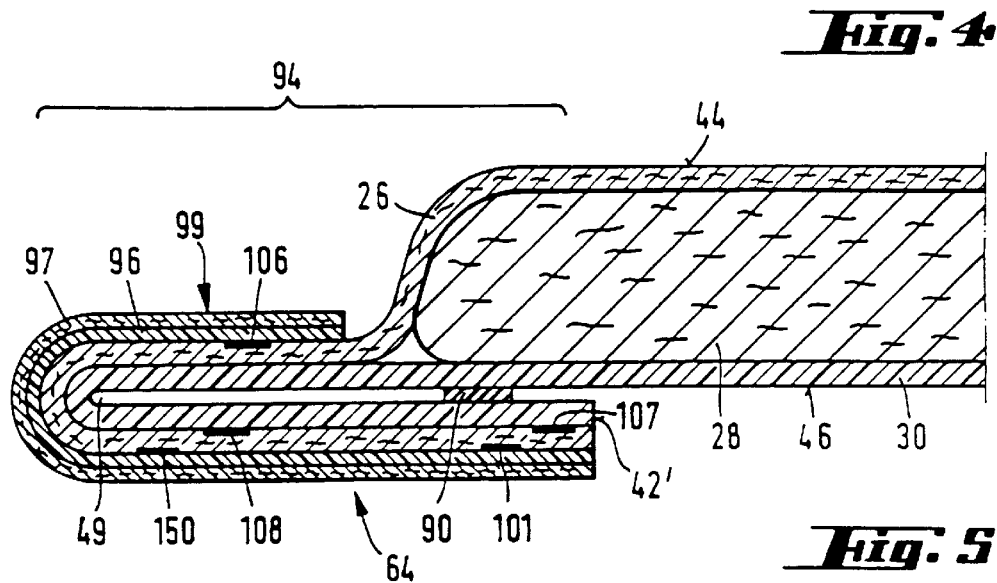
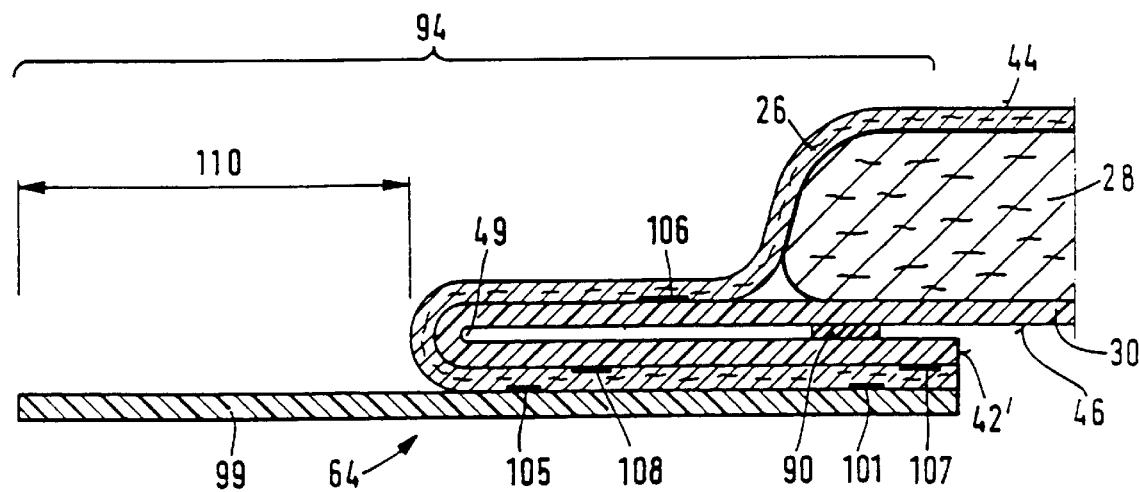

DISPOSABLE ABSORBENT ARTICLE HAVING A FOLDED LANDING MEMBER FOR ENGAGING WITH A HOOK-TYPE FASTENING MEMBER

FIELD OF THE INVENTION

The invention relates to disposable absorbent articles comprising a mechanical fastening system.

Such disposable absorbent articles are known from EP-A-0 321 234.

Known mechanical fastening systems for use in disposable absorbent articles comprise hook-type tape tabs in the back waist region which mechanically engage with a landing member. The landing member is a loop-type material which is located in the front waist region and which entangles with the hooks of the tape tabs to form a closure having resistance against peel forces and shear forces.

The known absorbent articles may comprise a landing member which is positioned in a region of the backsheet to engage the hook-type tape tabs when the article is placed in a rolled-up disposal configuration.

The loop-type materials used for the landing members of the known mechanical fastening systems are relatively expensive materials.

Another drawback of the addition of separate patches or strips of loop-type material to the backsheet, is an increase in the complexity of the production process for making an absorbent article.

Furthermore, it is difficult to attach patches or strips of loop-type material to the garment-facing side of an absorbent article in the front waist region when the front waist region is elasticated, or is made of an elastically extensible material, such that the material in the front waist region is gathered. The patches of loop-type material, which are non-elastic, may impair the elastic properties of the front waist region.

It is therefore an object of the present invention to provide an absorbent article having a mechanical closing system which is of simple construction and which is cost-effective.

It is a further object of the present invention to provide an absorbent article having a loop-type mechanical landing member which can effectively and firmly adhere to or be a part of an elasticacted waist region, without impairing the elasticity thereof.

SUMMARY OF THE INVENTION

The absorbent article according to the present invention comprises a backsheet having a garment-facing side and a user-facing side, two longitudinal sides, a front transverse edge, a front waist region located along the the front transverse edge, a back transverse edge end, and a back waist region located along the back transverse edge. The mechanical fastening system of the article comprises at least two hook-type fastening members located in the back waist region. A landing member for mechanically engaging with the hook-type fastening member is located in the front waist region. An inner layer covers at least a part of the user-facing side of the backsheet in the front waist region. The inner layer is doubled-over along a fold line in the front waist region such that the the inner layer is turned outwardly to the garment-facing side and forms the landing member. The material of the inner layer is adapted to mechanically engage with the hook-type fastening members. Attachment means are provided for keeping the region of the front waist edge of the inner layer against the backsheet in a doubled-over configuration.

The inner layer may extend beyond the front transverse edge of the backsheet and may be doubled-over onto the backsheet along the backsheet's front transverse edge. Alternatively, the inner layer may be co-extensive with the backsheet, both the backsheet and the inner layer being doubled-over in the front waist region.

By turning the inner layer that is located on the user-facing side of the backsheet, outwardly, a landing member is obtained in a simple manner. No additional loop-type materials other than those normally used in diaper manufacturing, need be attached to form the landing member.

The landing member which is formed by the material of the inner layer is flexible and can elastically contract and expand to conform to the movements of the wearer. The conformability of the loop-type fastening member according to the invention to the geometry of the wearer in the front waist region, is especially advantageous when elastic elements are located in the front waist region to provide a snug fit of the article around the waist of the wearer.

The inner layer, which for instance comprises a fibrous non-woven layer, may be the topsheet which covers the absorbent core or may be a layer located between the topsheet and the backsheet to form a barrier against leakage from the front transverse edge of the absorbent core (a so-called waist shield layer). Alternatively, the inner layer may be a layer which is located below the absorbent core and which is co-extensive with the backsheet in the front waist region or may be a high wet-strength tissue which envelops the core. By selecting the hook-type fastening members to match the non-woven material that is regularly employed as an inner layer, the hooks can mechanically engage with this layer to fasten the absorbent article on a wearer.

For fibrous inner layers having relatively little surface irregularities, relatively small and sharply pointed hooks will be required for the hook-type material of the hook-type fastening members to be able to engage with such a layer. For non-woven sheets or tissues which comprise a relatively large number of protruding loops at their surface, the hooks of the hook-type material may be of larger size and may be relatively flexible to obtain mechanical attachment to such sheets or tissues. Alternatively, the surface texture of the inner layers can be selected to match a given type of hook-fastening material to achieve proper fastening. The inner layer may be mechanically treated to impart the desired surface characteristics which ensure proper attachment to a pre-determined type of hook material.

Is one embodiment of an absorbent article according to the invention an elastic element may be comprised on the inner layer for instance on the topsheet along the front waist edge. The use of the elastic element in the region of the landing member has as an advantage that the material of the landing member is contracted to form gathers, which provide improved attachement with the hook material of the hook-type fastening members.

The backheet may be comprised of a non-woven material, a thermoplastic film or a laminate of a non-woven material and a film. The backsheet may be formed of an elastic material. There may be additional layers located between the topsheet and the backsheet.

In another embodiment of an article according to the invention, at least two cuts extend through the backsheet and the inner layer from the front waist edge, in the direction of the back waist edge, wherein the part of the front waist region of the backsheet which extends between the cuts is doubled-over.

By doubling-over the backsheet along these cuts, a low-cut foldline of the front waist region can be obtained which fits well below the belly of the wearer in the so-called "low motion zone". Preferably, a number of cuts extend radially from the front waist edge to an inwardly concave fold line, such that a number of backsheet-material sections are formed which are each folded along the concave fold line. In this manner a shaped front transverse edge and the landing member are formed simultaneously.

In one embodiment of an absorbent article according to the invention, the longitudinal sides in the back waist region have a rounded section which matches with the fold line in the front waist edge when the article is put on a wearer.

The combination of the rounded sections of the longitudinal edges and the low-cut front waist region provide room for comfortably fitting around the belly of the wearer.

Preferably, additional hook-type fastening elements are provided on the front waist region to engage with the loop-type material of the back waist region. The relatively low position of the additional hook-type fastening elements on the doubled-over section of the front waist region, places them below the rounded edges of the transverse sides and allows for proper fastening of these additional hook-type elements without a need for increasing the width of the backsheet material in the front waist region.

BRIEF DESCRIPTION OF THE DRAWINGS

The invention will be described in detail with reference to the accompanying drawings. In the drawings:

FIGS. 3–8 show cross-sectional views through the front waist region along a line of cross-section parallel to the longitudinal centerline, of different embodiments of landing members according to the invention.

DETAILED DESCRIPTION OF THE INVENTION

Mechanical closing systems of the present invention are useful and beneficial when applied to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body and which are intended to be discarded after a single use (i.e., they are not intended to be laundered or otherwise restored or reused). A preferred embodiment of the disposable absorbent article of the present invention is a diaper 20. As used herein, the term "diaper" refers to a garment generally worn by infants or incontinent persons that is drawn up between the legs and fastened about the waist of the wearer. Examples of the kinds of diapers to which the present invention is very readily adapted are shown in the above-referenced U.S. Pat. Re. No. 26,151 issued to Duncan et al. and in U.S. Pat. No. 3,860,003 entitled "Contractable Side Portions for Disposable Diaper" which issued to Kenneth B. Buell on Jan. 14, 1975.

It will be apparent form the following description that the mechanical fastening system illustrated and described herein may be applied to the body portion of such diapers. On the other hand, it will be understood that the invention is not limited to any specific diaper structure or configuration.

Figure 1:
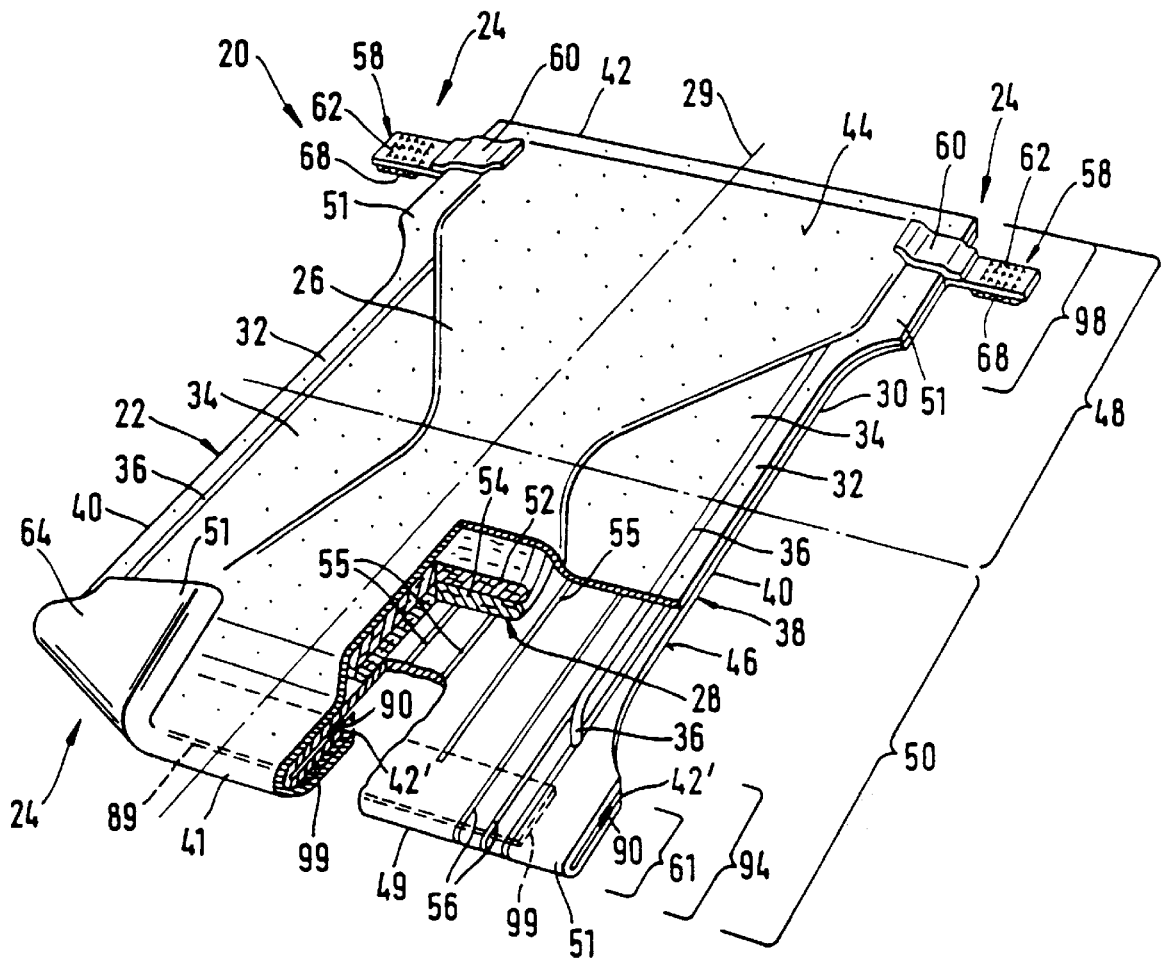
FIG. 1 shows a partially cut-away perspective view of a disposable diaper comprising a landing member according to the invention.

Referring to the drawings, it will be noted that FIG. 1 is a partially cut-away perspective view of the diaper 20 of the present invention prior to its being placed on the diaper wearer by the diaper user. As can be seen in FIG. 1, a preferred diaper 20 comprises a body portion 22 and a fastening system 24. A preferred body portion 22 comprises a liquid pervious topsheet 26, an absorbent core 28, a liquid impervious backsheet 30, and elastically contractible leg cuffs 32 comprising a side flap 34 and one or more elastic members 36. While the topsheet 26, the absorbent core 28, the backsheet 30, the side flaps 34, and the elastic members 36 may be assembled in a variety of well-known configurations, a preferred disposable diaper configuration is shown and described generally in the above-referenced U.S. Pat. No. 3,860,003 which issued to Kenneth B. Buell on Jan. 14, 1975.

FIG. 1 shows a preferred embodiment of the body portion 22 in which the topsheet 26 and the backsheet 30 are coextensive and have length and width dimensions generally larger than those of the absorbent core 28. The topsheet 26 is superposed on the backsheet 30 thereby forming the periphery 38 of the body portion 22. The periphery 38 defines the outer perimeter or, in other words, the outer extend of the body portion 22. The periphery 38 comprises longitudinal sides 40, back transverse edge 42, and fold line 49 along which the topsheet 26 and the backsheet 30 are doubled over to form landing member 64. The body portion 22 has user-facing side 44 and garment-facing 46. In general, the garment-facing side 46 of the diaper 20 extends from back transverse edge 42 to fold line 49 of the diaper and from one longitudinal side 40 to the other longitudinal side 40 of the diaper and is the surface farthest from the wearer during use of the diaper 20. The garment-facing side of any layer comprised in the diaper 20 is the side of the layer farthest from the wearer during use. When a backsheet 30 is used, it typically forms the larger part of the garment-facing side 46 of the body portion 22. The user-facing side 44 is that surface of the diaper opposite the garment-facing side 46 and in the embodiment shown is typically formed by the topsheet 26. In general, the user-facing side 44 of the diaper 20 is that surface coextensive with the garment-facing side 46 and which is for the greater part in contact with the wearer when the diaper 20 is worn. For any layer comprised in the diaper 20, the user-facing side is that side of the layer located closest to the wearer during use.

The diaper 20 has first and second end regions 48 and 50, respectively, extending from the back transverse edge 42, and the fold line 49 of the diaper periphery 38 toward the transverse centerline of the diaper 20. Both the first end region 48 and the second end region 50 extend a distance of about one-half of the length of the diaper 20 such that the end regions comprise each half of the diaper 20.

Both the first end region 48 and the second end region 50 have panels 51. The panels 51 are those portions of the first end region 48 and the second end region 50 which overlap when the diaper 20 is fastened about the waist of the wearer. The extent to which the end regions overlap and thus the extent to which the panels 51 are formed will depend on the overall dimensions and shape of the diaper 20 and the size of the wearer.

The absorbent core 28 of the body portion 22 may be any means which is generally compressible, conformable, non-irritating to the wearer's skin, and capable of absorbing and retaining liquids and certain body exudates. The absorbent core 28 may be manufactured in a wide variety of sizes and shapes (e.g., rectangular, hourglass, asymmetric, etc.) and from a wide variety of liquid absorbent materials commonly used in diapers and other disposable absorbent articles, such as comminuted wood pulp which is generally referred to as the airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 28 should, however, be compatible with the design exudate loading in the intended use of the diaper 20. Further, the size and absorbent capacity of the absorbent core 28 may varied to accommodate wearers ranging from infants to adults.

While the absorbent core 28 may comprise a single layer of absorbent material such as the configuration described in U.S. Pat. No. 4,610,678 entitled "High-Density Absorbent Structure" which issued to Paul T. Weisman and Steven A. Goldman on Sep. 9, 1986 a preferred embodiment of the absorbent core 28 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on Jun. 16, 1987, having an asymmetric-shaped upper layer 52 and a lower layer 54. The upper layer 52 preferably acts as a liquid acquisition/distribution layer comprised primarily of hydrophilic fiber material. The lower layer 54 acts as a liquid storage layer comprised of a mixture of hydrophilic fiber material and particles of an absorbent gelling material (hydrogel material).

Both the upper layer 52 and the lower layer 54 preferably comprise an absorbent layer encased in a tissue layer. It should be understood, however, that the size, shape, configuration, and total absorbent capacity of the upper layer 52 or the lower layer 54 may be varied to accommodate wearer's ranging from infants through adults. Therefore, the dimensions, shape, and configuration of both the upper layer 52 and the lower layer 54 may be varied (e.g., the upper layer or the lower layer may have a varying caliper, a hydrophilic gradient, a rapid acquisition zone or may contain absorbent gelling material).

The absorbent core 28 is superposed on the backsheet 30 and is preferably associated thereto by a core attachment means 55 such as those well known in the art, for example, pressure-sensitive adhesives, hot melt adhesives or other adhesives; ultrasonic bonding; or heat/pressure sealing. The absorbent core 28 may be secured to the backsheet 30 by a uniform continuous layer of adhesive, a patterned layer of adhesive, or any array of separate lines or spots of adhesive. And adhesive which has been found to be satisfactory is preferably a hot-melt adhesive such as manufactured by Eastman Chemical Products Company of Kingsport, Tennessee and marketed under the tradename of Eastobond A-3 or by Century Adhesives, Inc., of Columbus, Ohio and marketed under the tradename Century 5227. The core attachment means 55 preferably comprise an open pattern network of filaments of adhesive as is shown in U.S. Pat. No. 4,573,986 entitled "Disposable Waste-Containment Garment" which issued to James A. Minetola and David R. Tucker on Mar. 4, 1986.

The backsheet 30 is impervious to liquids and is preferably manufactured from a thin plastic film, although other flexible liquid impervious materials may also be used. The backsheet 30 prevents the exudates absorbed and contained in the absorbent core 28 from soiling articles which contact the diaper 20 such as bedsheets and undergarments. Preferably, the backsheet 30 is a polyethylene film having a thickness of from 0.012 mm (0.5 mil) to 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 30 is preferably embossed and/or matte finished to provide a more clothlike appearance. Further, the backsheet 30 may permit vapors to escape from the absorbent core 28 while still preventing exudates from passing through the backsheet 30.

The size of the backsheet 30 is dictated by the size of the absorbent core 28 and the exact diaper design selected. In a preferred embodiment, the backsheet 30 has a modified hourglass shape extending beyond the absorbent core a minimum distance of at least 1.3 cm to 2.5 cm (0.5 to 1.0 inch) around the entire diaper periphery 38.

The topsheet 26 of the body portion 22 of the present invention is compliant, soft feeling, and non-irritating to the wearer's skin. Further, the topsheet 26 is liquid pervious permitting liquids to readily penetrate through its thickness. A suitable topsheet 26 may be manufactured from a wide range of materials such as porous foams, reticulated foams, apertured films, natural fibers (e.g. wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 28.

A particularly preferred topsheet 26 comprises staple length polypropylene fibers having a denier of about 1.5, such as Hercules Type 151 polypropylene fibers marketed by Hercules, Inc. of Wilmington, Del. As used herein, the term "staple length fibers" refer to those fibers, having a length of at least 15.9 mm (0.625 inches).

There are a number of manufacturing techniques which may be used to manufacture the topsheet 26. For example, the topsheet 26 may be woven, non-woven, spunbonded, carded, hydroformed or the like. A preferred topsheet 26 is carded and thermally bonded by means well-known to those skilled in the fabric art. Preferably, the topsheet 26 has a basis weight from 15 to about 30 grams per square meter, a minimum dry tensile strength of at least 400 grams per centimeter in the machine direction and a wet tensile strength of at least 55 grams per centimeter in the cross-machine direction.

The topsheet 26 and the backsheet 30 are associated together in any suitable manner as is well known in the diaper manufacturing art. As used herein, the term "associated" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members which in turn are affixed to the backsheet 30. In a preferred embodiment, the topsheet 26 and the backsheet 30 are joined directly to each other in the diaper periphery 38 by a flap attachment means 56 such as an adhesive or any other attachment means as is known in the art. In general, the core attachment means 55 that affixes the absorbent core 28 to the backsheet 30 is the same means as the flap attachment means 56 that affixes the topsheet 26 to the backsheet 30. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

Elastically contractible leg cuffs 32 are disposed adjacent the periphery 38 of the body portion 22, preferably along each longitudinal edge 40, so that the leg cuffs 32 tend to draw and hold the diaper 20 against the legs of the wearer. While the leg cuffs 32 may comprise any of several means as are well known in the diaper art, a particularly preferred leg cuff construction comprises a side flap 34 and one or more elastic members 36, as is described in detail in the hereinbefore referenced U.S. Pat. No. 3,860,003. In addition, a method and apparatus suitable for manufacturing a disposable diaper having elastically contractible leg cuffs are described in U.S. Pat. No. 4,081,301 entitled "Method and Apparatus For Continuously Attaching Discrete, Stretched Elastic Strands to Predetermined Isolated Portions of Disposable Absorbent Articles" which issued to Kenneth B. Buell on Mar. 28, 1978.

In a preferred embodiment, the elastically contractible leg cuff 32 comprises a side flap 34 and an elastic member 36 comprising an elastic thread.

The diaper 20 is provided with a fastening system 24 for forming a side closure. Thus, the diaper 20 is fitted to the wearer and the first end region 48 and the second end region 50 are maintained in an overlapping configuration when the diaper 20 is worn.

In a preferred embodiment of the present invention as shown in FIG. 1, the fastening system 24 comprises fastening members 58, preferably comprising a tape tab 60 and a hook-type fastening element 62, disposed adjacent each longitudinal side 40 of the body portion 22 in the back waist region 98 of the first end region 48; a landing member 64, engageable with the hook-type fastening element 62, disposed on the outside surface 46 of the body portion 22 in the front waist region 94. The landing member 64 is formed by folding the topsheet 26 and the backsheet 30 around fold line 49, and attaching the doubled-over front waist region of the backsheet to the main backsheet portion with attachment means 90. Additional fastening/disposal means 68 may be positioned on the tape tab 60, for allowing the diaper 20 to be secured in a disposal configuration so as to provide convenient disposal of the diaper 20.

Each fastening member 58 is intended to provide a mechanical fastening means for engaging the landing member 64 so as to provide a secure side closure for the diaper 20.

The fastening members 58 comprises combination of a hook-type fastening element and adhesive attachment means positioned on the body portion 22 of the diaper 20. The hook-type fastening element 62 of each fastening member 58 is joined to the body portion and preferably covers an area 25 mm wide (i.e., generally perpendicular to the longitudinal centerline 29) by 62.5 mm long (i.e., generally parallel to the longitudinal centerline 29) at the panels 51 of the body portion 22. An exemplary embodiment of a hook-type fastening member 62 is described in U.S. Pat. No. 4,699,622 entitled "Disposable Diaper Having an Improved Side Closure" issued to John W. Toussant and Margaret H. Hasse on Oct. 13, 1987.

Figure 2:
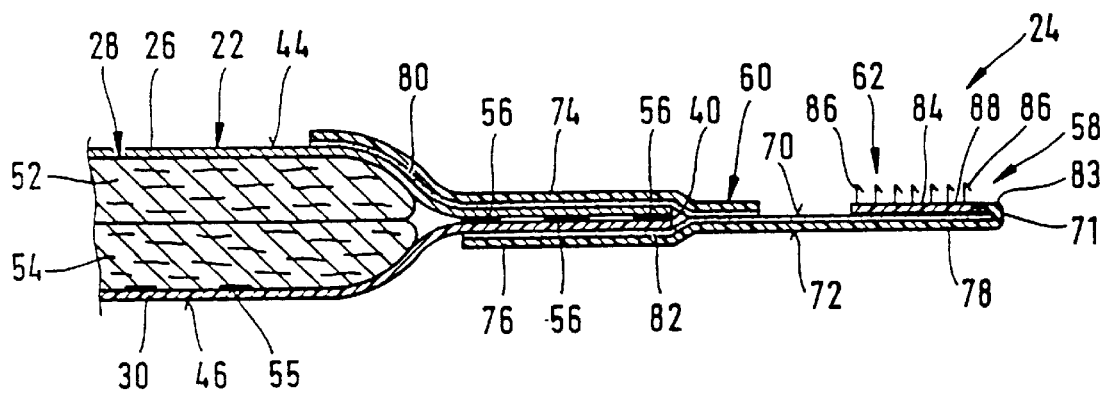
FIG. 2 shows a cross-sectional view through a hook-type fastening member of FIG. 1 along a line of cross-section parallel to the back transverse edge.

As shown in FIGS. 1 and 2, the fastening member 58 most preferably comprises a tape tab 60. Any of the well known configurations and constructions of a tape tab may be used. A preferred tape tab 60 is a Y-shaped tape tab as described in detail in GB-A-1458566. Alternatively preferred tape tabs are described in detail in co-pending European Patent Application No. 87300450.1.

A particularly preferred tape tab 60 is illustrated in FIG. 2 and has a fastening surface 70 and a backing surface 72. The fastening surface 70 is that surface of the tape tab 60 designed to engage the landing member 64 of the present invention. Thus, the fastening surface 70 of the tape tab 60 will generally correspond to the garment-facing side 44 of the body portion 22. The backing surface 72 is that surface opposite of the fastening surface 70 and generally corresponds to the outside surface 46 of the body portion 22. The backing surface 72 is thus generally exposed during wear of the diaper 20.

The preferred tape tab 60 illustrated in FIG. 2 is one which is anchored to both the user-facing side 44 and the garment-facing side 46 of the body portion 22 to create a manufacturer's end (i.e., that attachment of the tape tab 60 to the diaper 20 made during manufacture of the diaper 20). The tape tab 60 has another element which forms the user's end i.e., that joint made by the person in securing the diaper to the wearer). Thus, the preferred tape tab 60 of the present invention has at least three elements, a first fixed portion 74, a second fixed portion 76, and a connective portion 78. The first fixed portion 74 is that portion of the tape tab 60 which is attached to the user-facing side 44 of the body portion 22. The second fixed portion 76 is that portion of the tape tab 60 which is attached to the garment-facing side 46 of the body portion 22. The first fixed portion 74 and the second fixed portion 76 thus form the manufacturer's end of the tape tab 60. The connective portion 78 is that portion of the tape tab 60 which is attached to another portion of the diaper 20, generally the landing member 64 by the user when securing the diaper 20 on the wearer. The connective portion 78 thus forms the user's end. Additionally, the outer surface of the second fixed portion 76 and the outer surface of the connective portion 78 form the backing surface 72 of the tape tab 60 while the inner surface of the first fixed portion 74 and the inner surface of the connective portion 78 form the fastening surface 70 of the tape tab 60.

The preferred Y-shaped tape tab 60 of the present invention can be constructed in several ways. The first fixed portion 74, the second fixed portion 76, and the connective portion 78 can each be separate tapes which meet and are joined adjacent the longitudinal edge 40 of the body portion 22 in an area of joinder. A more practical structure for the tape tab 60 is one in which the connective portion 78 and either the first fixed portion 74 or the second fixed portion 76 are a unitary strip of tape material. If the connective portion 78 is unitary with the second fixed portion 76 as shown in FIG. 2, then the first fixed portion 74 is a separate element which is attached to the combined connective portion and the second fixed portion adjacent to the longitudinal side 40 of the body portion 22.

FIG. 2 also shows tab attachment means for securing the tape tab 60 to the body portion 22. These tab attachment means are any of those attachment means which provide an adequate bond, and preferably are any of the pressure-sensitive adhesives well-known to those of ordinary skill in the adhesive art. The outer surface of the first fixed portion 74 is affixed to the user-facing side 44 of the body portion 22 by a first tab attachment means 80. The inner surface of the second fixed portion 76 is affixed to the garment-facing side 46 of the body portion 22 by a second tab attachment means 82. The connective portion is provided with a first fastening element 62 joined to it preferably by the second tab attachment means 82 (alternatively, a third tab attachment means if the connective portion 78 is a separate element from the second fixed portion 76), although an adhesive attachment means may be placed on the first fastening element 62 separately and the combined material joined to the connective portion 78.

Preferred materials for the tape tabs 60 comprises a tape material such as tape code numbers XPF 14.43.0, Y-9376, or Y-9030 available from The Minnesota Mining and Manufacturing Company, St. Paul, Minn. The tape material in the embodiments are preferably a polyethylene film having a tab attachment means tailored to bond to the polyethylene positioned on the tape material. The tape tab attachment means may comprise any of those adhesives which provide an adequate bond with other portions of the diaper, and is preferably any of the pressure-sensitive adhesives well-known to those of ordinary skill in the art. Preferred tab attachment means is a pressure-sensitive adhesive such as code number XPF 1.42.34 available from The Minnesota Mining an Manufacturing Company, St. Paul, Minn.

As shown in FIG. 2, the tape tab 60 may also have a grip tab 83 at the distal edge 71 in the connective portion 78. The grip tab 83 may be formed by folding over a small margin of the distal edge 71 of the connective portion 78 and attaching it to itself. This forms an end on the connective portion 78 which is easier to grasp by the diaper user when the diaper 20 is to be fitted and attached to the wearer. The grip tab 83 is most beneficial when used when the connective portion 78 is superposed on the first fixed portion 74.

The hook-type fastening element 62 of the present invention comprises a hook fastening material 84. As used herein, the term "hook fastening material" is used to designate a material having engaging elements 86. It should also be understood that the use of the term "hook" should be non-limiting in the sense that the engaging elements 86 may comprise any shapes as are known in the art so long as they are adapted to engage a complementary second fastening element 66. As shown, the hook fastening material 84 preferably comprises a base 88 having a first surface and a second surface and a plurality of engaging elements 86 extending from the first surface of the base 88. Each of the engaging elements 86 are shown to comprise a stem supported at one end on the first surface of the base and an enlarged head positioned at the end of the stem opposite of the base.

The hook fastening material 84 of the present invention is intended to engage fibrous elements of fibrous material on the user-facing side 44 of the backsheet, which fibrous material may for instance be formed by the topsheet 26 or by a waist shield 91. Thus, the hook fastening material 84 may be manufactured from a wide range of materials. Suitable materials include nylon, polyester, polypropylene, or any combination of these materials. A suitable hook fastening material 84 comprises a number of shaped engaging elements 86 projecting from a woven backing such as the commercially available material designated "Scotchmate" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in C. Locke Scripps' co-pending U.S. patent application Ser. No. 07/007,841 entitled "Disposable Diaper Having An Improved Fastening Device" filed Jan. 26, 1987.

Other suitable hook-type materials for use in the present invention are for instance extruded hooks available under the reference MC5 from the Minnesota Mining and Manufacturing Company, ST. Paul, Minn. or printed hooks available from the same company under references CS200 and MC6. Other suitable hook-type materials are available under reference 942 or 960E from Aplix, Inc., P.O. Box 7505, Charlotte, N.C. 28241.

The landing member 64 comprises a loop-type material such as for instance the fibrous topsheet material. As used herein, the term "loop-type" material is intended to mean any fibrous material which can mechanically engage with the hook-type material of the fastening members 58 to maintain the diaper 20 affixed around the waist of a wearer. Suitable loop-type material is described in U.S. Pat. No. 5,326,612 (Goulait).

Other suitable loop-type materials for use in the present invention may comprise woven materials such as brushed loops available from Texmaille S.A., Rue Pasteur, 02610 Moy de L'aisne, France; double knit loops available from Tissages de Quintenas S.A., Parc d'activitls de marenton, B.P.158-07104 Annonay, France; and Linerless loops available under reference LLL from the Minnesota Mining and Manufacturing Company.

Again other suitable loop-type materials are formed by non-woven materials.

In general, the materials of the hook-type fastening members 58 and the loop-type landing member 64 should be selected such that the peel force of a 30 mm wide patch of hook-type material is between 3 and 20 N, preferably about 7–8 N and the shear force of a patch of hook-type material of dimensions of 30×13 mm is between 10 and 100 N, preferably about 50 N.

The tests for measuring the peel forces and the shear forces exerted by the hook-type fastening members 58 on the loop type landing member 64 are described below.

I. 135°—Peelforce Test

This method describes the procedure for measuring the peel force, in grams, of the combined hook-type fastening member and loop-type landing member. The materials under test are mounted on a steel plate-sled assembly and are separated at a constant peel angle of 135°.

During the test the temperature is maintained at 73°±20° F. The relative humidity is controlled at 50±2%.

A patch of loop-type material measuring 2 in.×4 in. is placed on a 2 in.×8 in.×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined towards the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted into an INSTRON test apparatus, Model 4201, which is set to have a cross-head speed of 12 in./minute and a Load Cell of 1 kg.

The steel plate is slidably mounted in a sled which is carried by the lower jaw of the INSTRON apparatus.

The leading edge of the tape tab 60 is placed in the upper jaw of the INSTRON apparatus.

The upper cross head is set in motion to pull the leading edge of the tape tab 60 off the loop-type landing member at an angle of 135° with respect to the loop-type landing member. The steel test plate on which the loop-type landing member is mounted, is moved in the sled consecutively with the cross head relative to the lower jaw to maintain a constant angle of 1350 during the full cycle of peeling off the tape tab.

The peak force, in grams, is recorded for at least four samples and is averaged.

II. 180° Shear Test

This method describes the procedure for measuring the shear force, in grams, of the combined hook-type fastening member and loop-type landing member. The materials under test are mounted on a steel plate and are separated at a constant peel-angle of 180°.

During the test the temperature is maintained at 73°±20° F. The relative humidity is controlled at 50±2%.

A patch of loop-type material measuring 2 in.×5 in. is placed on a 2 in.×5 in.×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined away from the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted horizontally into the lower jaw of an INSTRON test apparatus, Model 4201, which is set to have a cross-head speed of 12 in./minute, a Load Cell of 10.0 kg and a gage length of 2 in.

The leading edge of the tape tab 60 is placed in the upper jaw of the INSTRON apparatus.

The upper cross head is set in motion to pull the leading edge of the tape tab 60 off the loop-type landing member at an angle of 185° with respect to the loop-type landing member. When the maximum pull force has been reached, the crosshead is returned to the pre-set gage length.

The peak force, in grams, is recorded for at least four samples and is averaged.

FIG. 3 shows an embodiment wherein the landing member 64 comprises the topsheet 26, the backsheet 30 and an elastic element 99 comprised between the topsheet and the backsheet. The doubled-over combination of the topsheet, backsheet and elastic member, forms an elastically extendable landing member 64 comprising a number of gathers. The front waist region 94 of the backsheet 30 is attached to the main body of the backsheet by adhesive 90. Instead of adhesive attachment means 90, heat bonding, utrasonic bonding or pressure bonding may be used to maintain the front transverse edge 42' of the backsheet 30 in an inwardly folded position. The topsheet 26, the elastic element 99 and the backsheet 30 are all connected by adhesive connections 101,105,106,107, and 108, which may be formed by spiral glue patterns.

Preferably, the elastic element 99 provides a contractive force of between 20 and 250 g per 2.54 cm of the elastic element's width, at an elongation of 2.54 cm. The most preferred contractive force is about 150 g per 2.54 cm width at 2.54 cm elongation.

In the embodiment of FIG. 4, the elastic member 99 is, before doubling over along fold line 49, located on the user-facing side 44 of the topsheet 26. The elastic member 99 may in this case be comprised of a strechable non-woven material, which is adapted to engage with the hook-type fastening members. Alternatively, as shown in FIG. 4, the elastic member 99 may comprise a laminate of an elastomeric film 96 and a non-woven layer 97 attached to the elastomeric film. In this case the elastomeric film 96 of the elastic laminate is attached to the topsheet 26, the non-woven layer 97 of the elastic laminate being, before doubling over along fold line 49, located on the user-facing side 44 of the topsheet. When the front waist section 94 is doubled-over along fold line 49, the non-woven layer 97 of the elastic laminate will be located on the garment-facing side 46 of the backsheet 30 facing outwardly and forming the landing member 64.

In the embodiment of FIG. 5, the elastic element 99 comprises a segment 110 which is unattached to the underlying topsheet layer. Upon doubling-over of the topsheet 26 and the backsheet 30 along the fold line 49 in the front waist region 94, the unattached segment 110 of the elastic member 99 protrudes outwardly and forms a flexible and elastic waist panel, which will contact the stomach of the wearer during use.

Figure 6:
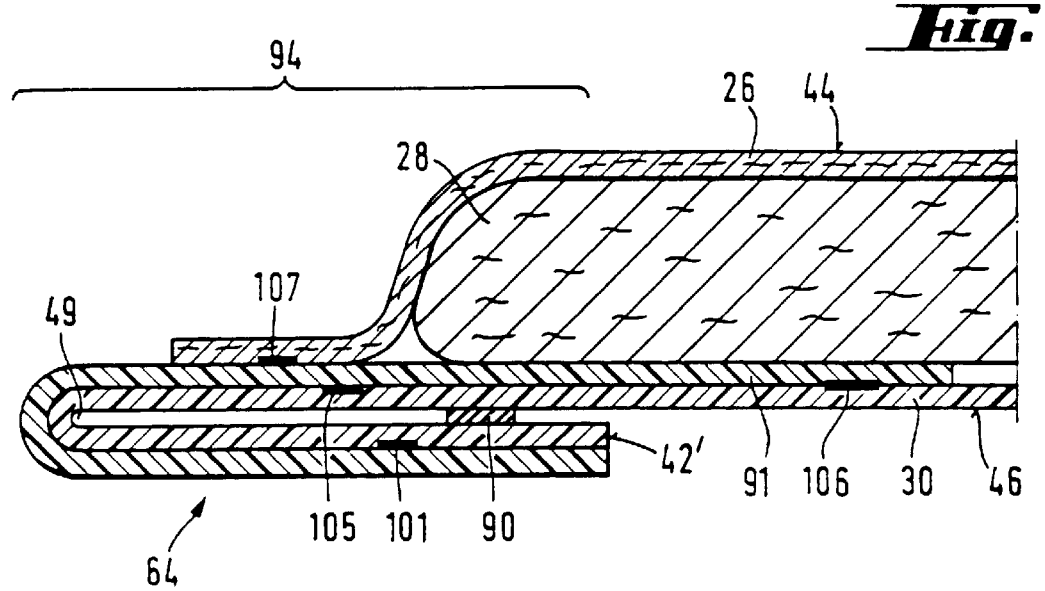

In the embodiment of FIG. 6, the inner layer that forms the landing member 64, comprises a layer 91 which underlies the core 28 and which is co-extensive with the user-facing side 44 of the backsheet 30. The inner layer 91 may be a core-reinforcement layer or may be the lower layer of an envelope layer which enwraps the core 28.

Figure 7:
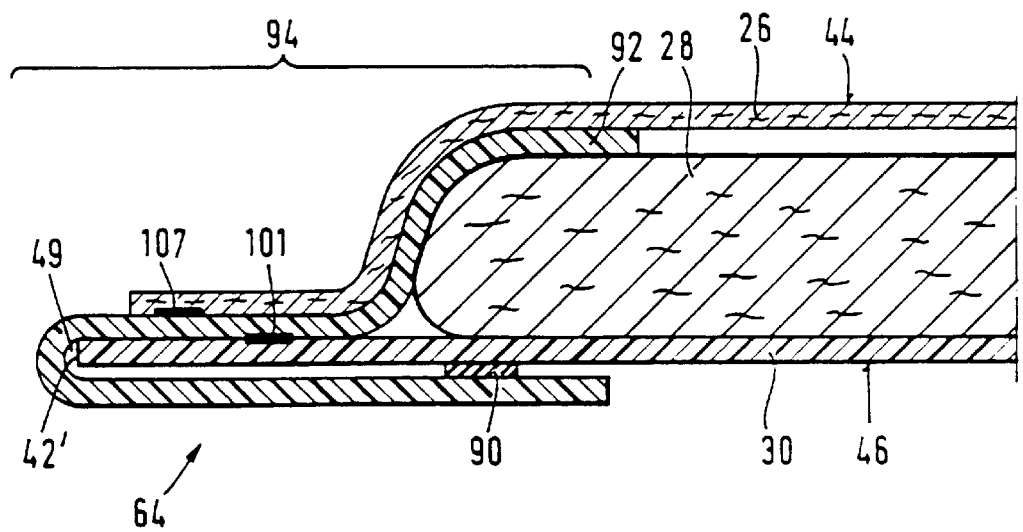

In the embodiment of FIG. 7, a fibrous waist shield 92 is located between the core 28 and the topsheet 26 along the front transverse region 94. The waist shield layer 92 extends beyond the front transverse edge of the topsheet 26 and the backsheet 30 and is attached to the backsheet in a doubled-over position by attachment means 90.

Figure 8:
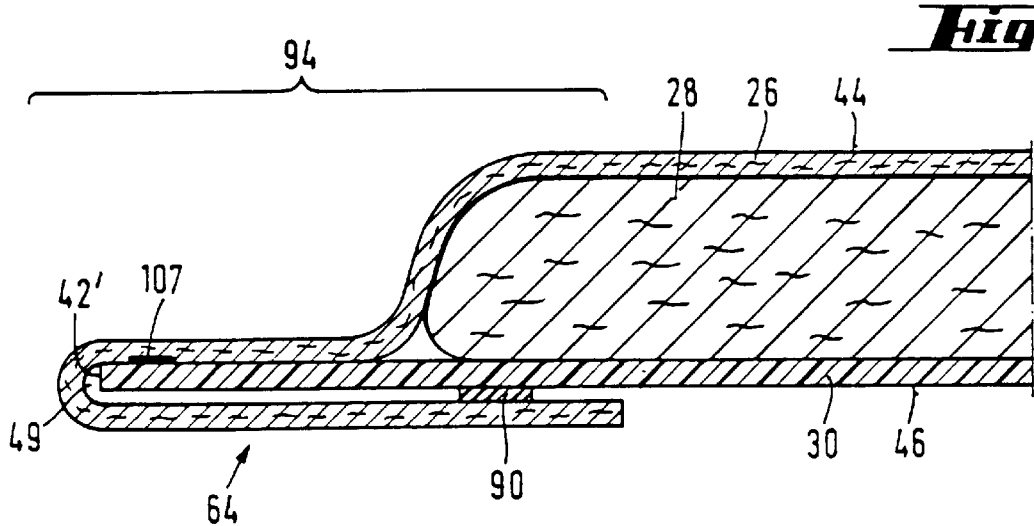

In the embodiment of FIG. 8, the topsheet 26 extends beyond the front transverse edge 42' of the backsheet, and is doubled over along the front transverse edge 42' to form the landing member. The folding line 49 and the front transverse edge 42' of the backsheet 30 coincide in this embodiment.

Figure 9:
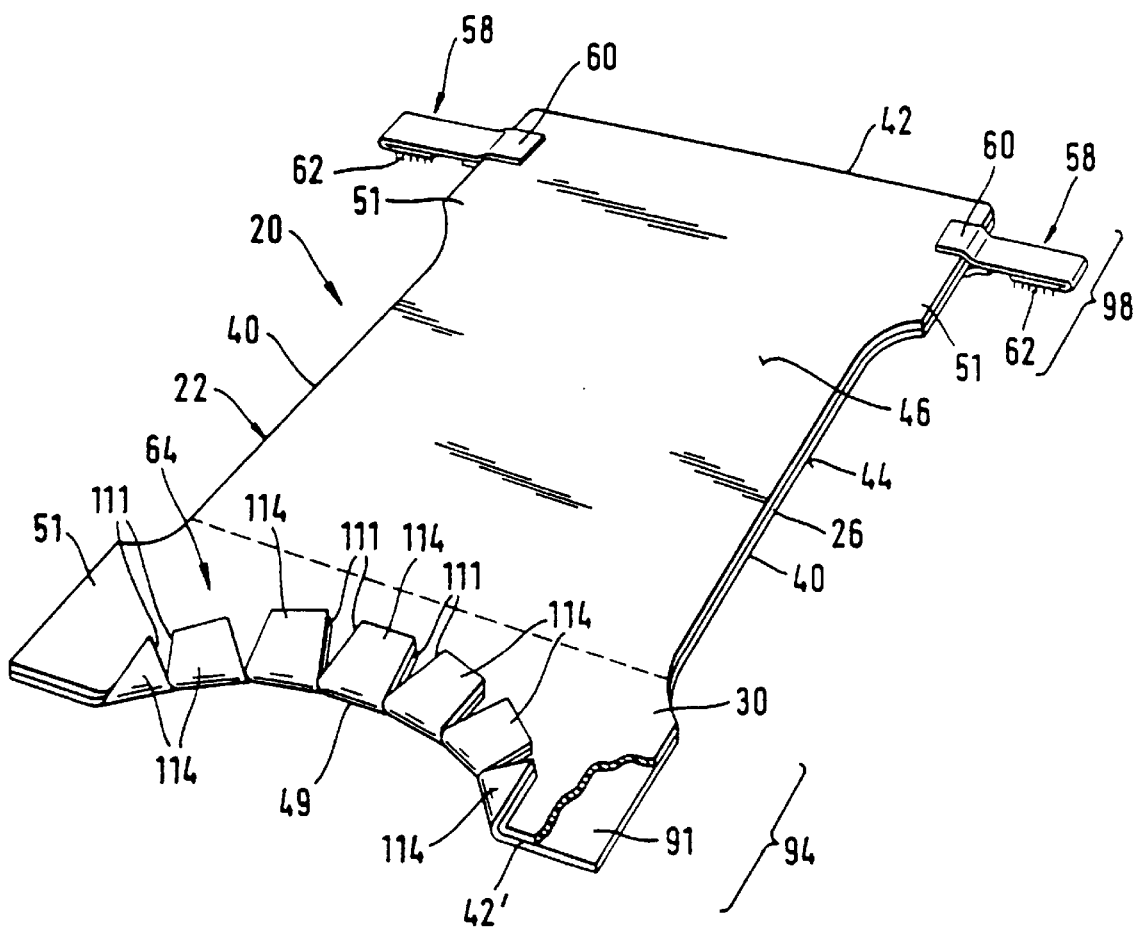
FIGS. 9–11 show a perspective view of the garment-facing side of absorbent articles having a number of cuts extending from the front transverse edge towards a fold line.
Figure 10:
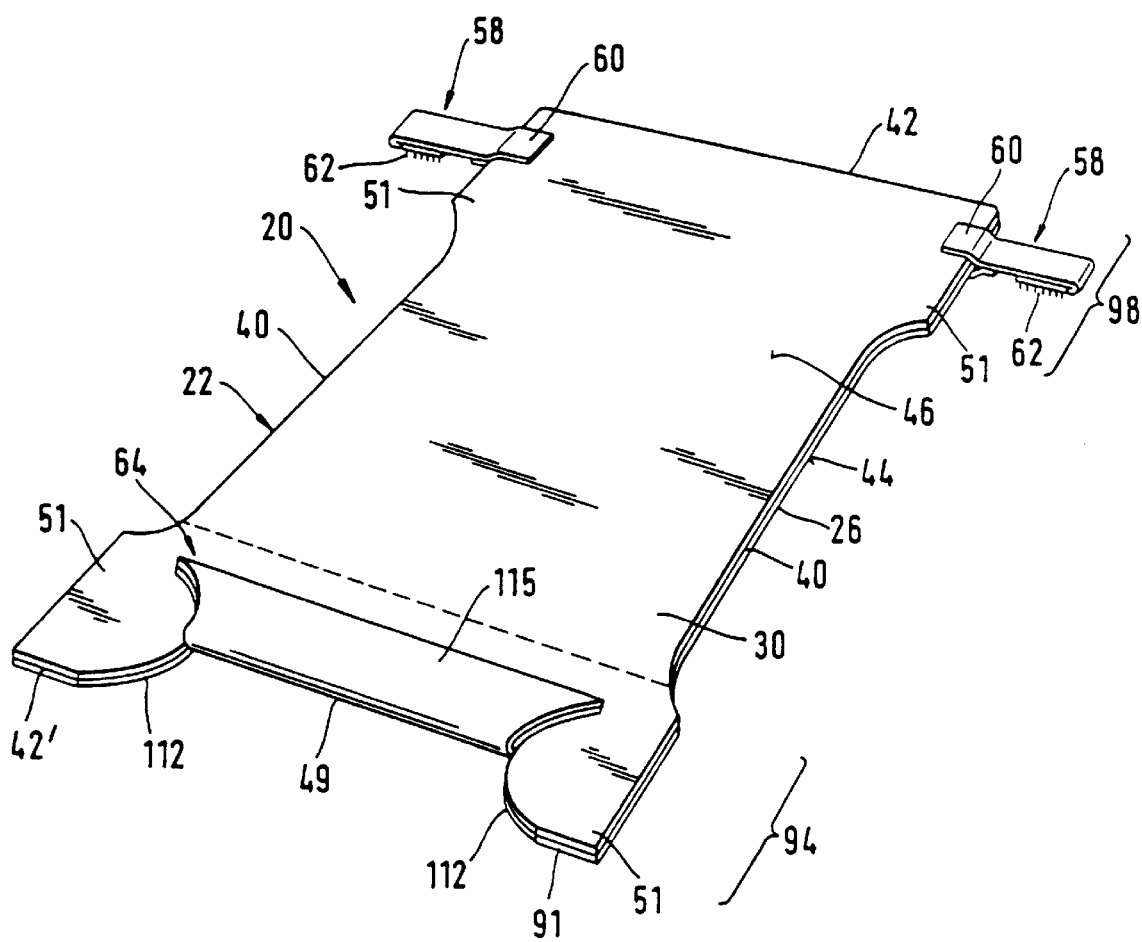
Figure 11:
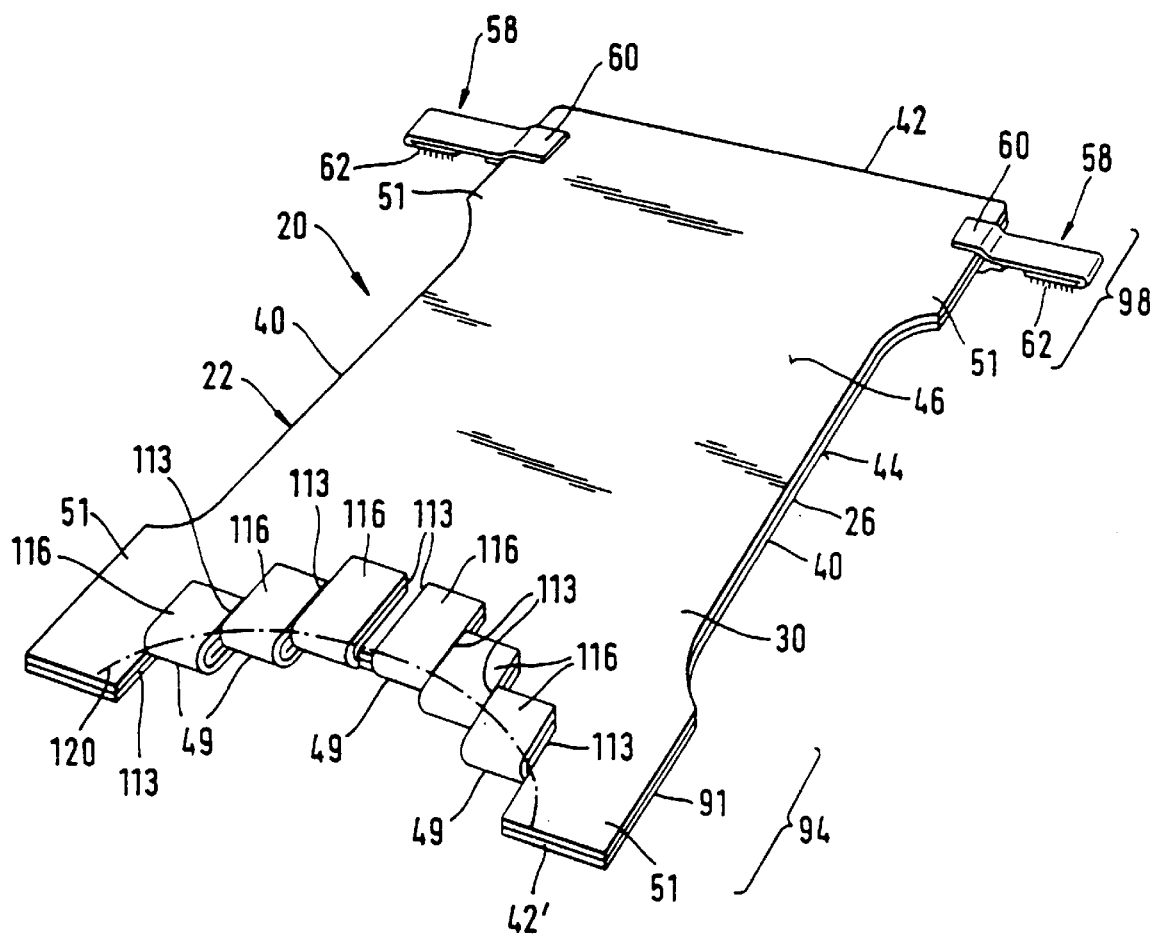

In the embodiment of FIG. 9, a number of cuts 111,112, 113 extend through the backsheet 30 and the inner layer 91 from the front transverse edge 42' towards an inwardly concave fold line 49. By the cuts 111,112,113, separate sections 114,115,116 and 117 are formed, each section extending between two adjacent cuts. The backsheet 30 and inner layer 91 of each section are folded along the fold line 49 to obtain a low-cut front waist region 94. In the embodiment of FIG. 10, the landing member 64 is formed by the doubled-over part of the front waist region 94 extending between two curved cuts 111,112. In the embodiment of FIG. 11, a number of cuts 111,112,113 extends in a direction generally parallel to the longitudinal sides 40. The fold line 49 for each section 114,115,116 is generally parallel to the transverse edges 42,42'. The folded-over sections 114,115, 116 result in a stepped front transverse edge. The stepped edge of the front waist region 94 may be cut along the contour 120 to obtain an inwardly concave waist region.

Figure 12:
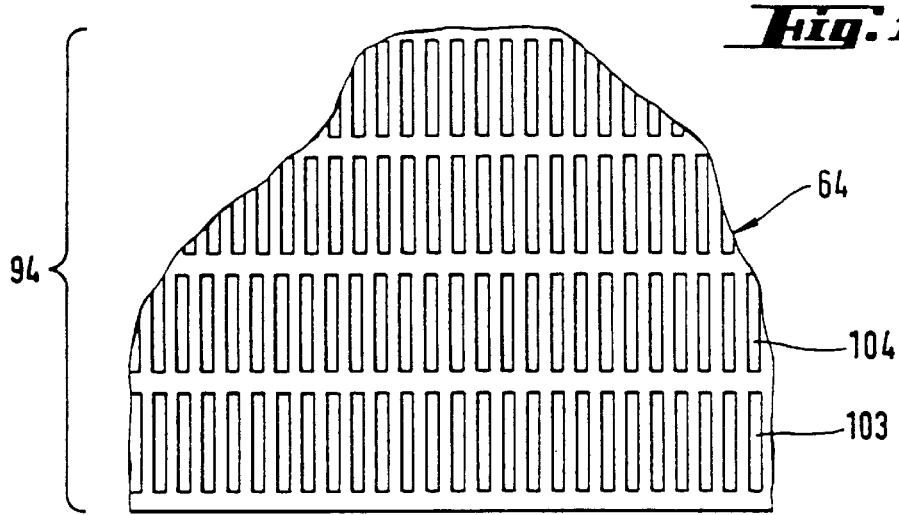
FIG. 12 shows a sectional plan view of a sheet having a number of extensible parallel corrugations.
Figure 13:
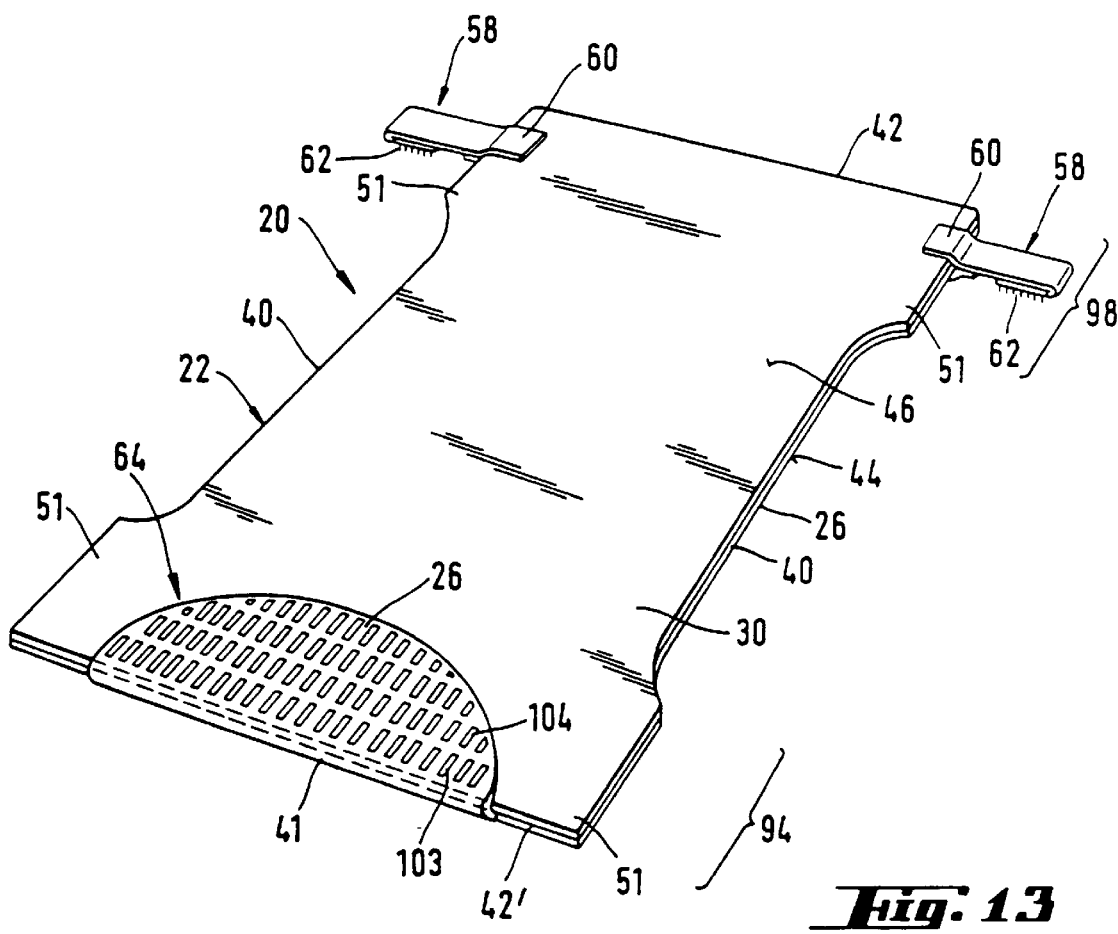
FIG. 13 shows the garment-facing side of an absorbent article, wherein the front waist region comprises parallel corrugations as shown in FIG. 13.

FIG. 12 shows an enlarged plan view of a landing member 64 comprising a number of parallel corrugations 103,104. The corrugations impart extensibility to the landing member 64, and cause the fibers of the landing member 64 to project outwardly and improve the mechanical fastening of the hook-type fastening members 58 thereto. The pattern of FIG. 12 may for instance be provided after doubling over of the topsheet onto the backsheet as shown in FIG. 13 and subsequently passing the front waist 94 region between two corrugated, intermeshing rolls, as described in U.S. Pat. No. 5,196,000 and U.S. Pat. No. 5,236,430.

Figure 14:
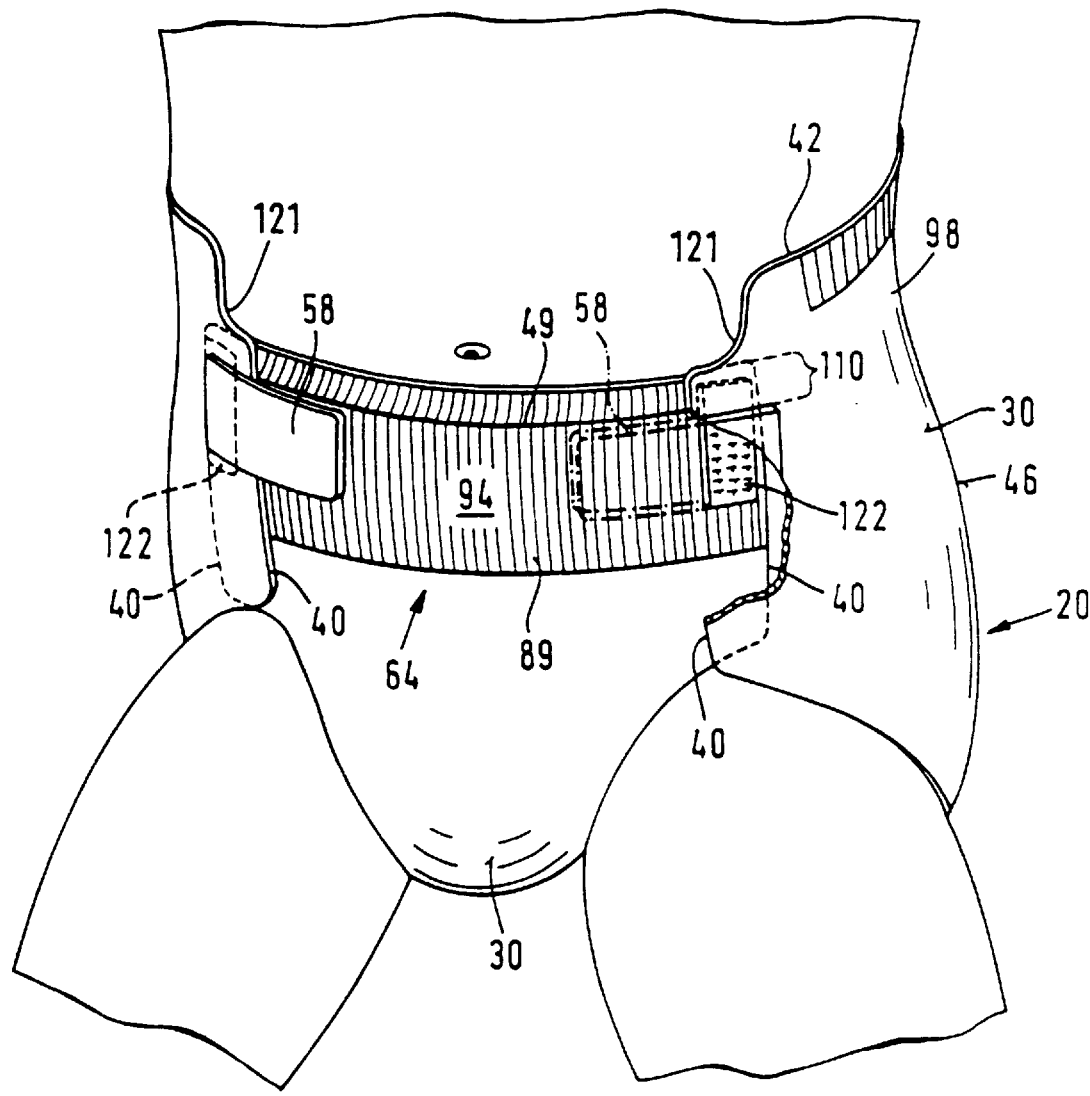
FIG. 14 shows a perspective view of a disposable absorbent article according to the invention when put on a wearer.

FIG. 14 shows a disposable absorbent article 20 when put on a wearer, the article comprising rounded sections 121 of the longitudinal sides 40. The rounded sections 121 match with the region of the fold line 49 and form a rounded contour. Additional patches of hook-type material 122 are located on the doubled-over landing member 64 to connect to the user-facing side (topsheet material) in the back waist region 98. The presence of the additional patches of hook-type material 122 helps to maintain the front and back end regions 48,50 of the article 20 in a properly overlapping relationship on the wearer.

What is claimed is:

1. An absorbent article comprising:
    a liquid pervious topsheet:
    a backsheet joined to at least a portion of the topsheet having a garment-facing side and a user-facing side, two longitudinal sides, a front transverse edge, a front waist region located along the front transverse edge, a back transverse edge, and a back waist region located along the back transverse edge;
    an absorbent core disposed between at least a portion of the topsheet and at least a portion of the backsheet;
    a mechanical fastening system comprising a hook-type fastening member located in the back waist region and extending transversely beyond each longitudinal side, and
    a landing member for mechanically engaging with the hook-type fastening member,
    the landing member including at least a portion of the topsheet which is doubled over the backsheet in at least a portion of the front waist region, the topsheet being adapted to mechanically engage with the hook-type fastening members; and
    attachment means for keeping the topsheet in a doubled-over configuration.

2. The absorbent article according to claim 1, wherein both the backsheet and the topsheet are doubled-over in the front waist (94) region, the attachment means keeping the front waist edge of the backsheet in a doubled-over configuration.

3. The absorbent article according to claim 2, comprising at least two cuts through the backsheet and the topsheet, the cuts extending from the front waist edge in the direction of the back waist edge, wherein the part of the front waist region of the backsheet and topsheet which extends between the cuts is doubled-over.

4. The absorbent article according to claim 3, wherein the topsheet is doubled-over along a foldline which forms an inwardly concave contour.

5. The absorbent article according to claim 1 wherein a topsheet is connected to at least a part of the user-facing side of the backsheet, the topsheet extending beyond the front transverse edge of the backsheet and being doubled over around the fold line onto the garment-facing side of the backsheet, the attachment means connecting the doubled-over topsheet to the garment-facing side of the backsheet.

6. The absorbent article according to claim 1, wherein the topsheet is contracted by an elastic element located along the front waist region.

7. The absorbent article according to claim 1, wherein the topsheet comprises of an elastomeric fibrous layer.

8. The absorbent article according to claim 1, wherein the backsheet comprises a thermoplastic film, and the topsheet comprises a non-woven material.

9. The absorbent article according to claim 1, wherein the longitudinal sides in the back waist region comprise a rounded section which matches with the region of the fold line when the article is put on a wearer.

10. The absorbent article according to claim 9, wherein the front waist region comprises in the region of each longitudinal side an additional hook-type material connected to the topsheet for attaching to a loop-type material located on the user-facing side of the back-waist region.

11. An absorbent article comprising:
    a liquid pervious topsheet,
    a laminate backsheet joined to at least a portion of the topsheet having first lamina forming a garment-facing side and a second lamina forming a user-facing side, two longitudinal sides, a front transverse edge, a front waist region located along the front transverse edge, a back transverse edge, and a back waist region located along the back transverse edge;
    an absorbent core disposed between at least a portion of the topsheet and at least a portion of the backsheet;
    a mechanical fastening system comprising
    a hook-type fastening member located in the back waist region and extending transversely beyond each longitudinal side, and
    a landing member for mechanically engaging with the hook-type fastening member, the landing member formed from at least a portion of the second lamina of the backsheet in the front waist region, wherein at least a portion of the second lamina is doubled-over along a fold line in the front waist region such that the second lamina is turned outwardly to form the landing member, at least a portion of the second lamina in the front waist region being adapted to mechanically engage with the hook-type fastening members; and
    attachment means for keeping the second lamina in a doubled-over configuration.

12. The absorbent article according to claim 11, wherein both the first lamina and the second lamina of the backsheet are doubled-over in the front waist region.

13. The absorbent article of claim 11 comprising at least two cuts through the backsheet, the cuts extending from the front waist edge in the direction of the back waist edge, wherein the part of the front waist region of the backsheet which extends between the cuts is doubled-over.

14. The absorbent article of claim 13, wherein the laminate of the backsheet is doubled-over along a foldline which forms an inwardly concave contour.

15. The absorbent article of claim 11, wherein the backsheet is contracted by an elastic element located along the front waist region.

16. The absorbent article of claim 11, wherein the first lamina of the backsheet comprises an elastomeric layer and the second lamina of the backsheet comprises a fibrous layer the fibrous layer being turned outwardly to form the landing member.

17. The absorbent article of claim 1, wherein the first lamina of the backsheet comprises a thermoplastic film and the second lamina of the backsheet comprises a non-woven material.

18. The absorbent article of claim 11, wherein the front waist region comprises in the region of each longitudinal side an additional hook-type material connected to the second lamina of the backsheet for attaching to a loop-type material located on the user-facing side of the back-waist region.

\* \* \* \* \*